United States Patent [19]
Haque et al.

[11] Patent Number: 6,132,756
[45] Date of Patent: *Oct. 17, 2000

[54] USE OF SANDALWOOD OIL FOR THE PREVENTION AND TREATMENT OF WARTS, SKIN BLEMISHES AND OTHER VIRAL-INDUCED TUMORS

[75] Inventors: Malika H. Haque; Azeez U. Haque, both of Columbus, Ohio

[73] Assignee: Haque, Inc., Columbus, Ohio

[ * ] Notice: This patent is subject to a terminal disclaimer.

[21] Appl. No.: 09/145,121

[22] Filed: Sep. 2, 1998

Related U.S. Application Data

[63] Continuation-in-part of application No. 08/960,303, Oct. 29, 1997, Pat. No. 5,945,116.
[60] Provisional application No. 60/030,307, Nov. 5, 1996.

[51] Int. Cl.$^7$ ............................... A61F 6/06; A61K 35/78
[52] U.S. Cl. ...................... 424/430; 424/195.1; 514/934; 514/967
[58] Field of Search ................................ 424/195.1, 430; 514/967, 934

[56] References Cited

U.S. PATENT DOCUMENTS

| | | |
|---|---|---|
| 4,908,355 | 3/1990 | Gettings et al. . |
| 5,532,215 | 7/1996 | Lexdey et al. ............................... 514/8 |
| 5,541,058 | 7/1996 | Kreider et al. ............................... 435/5 |
| 5,562,900 | 10/1996 | Boyer et al. ............................ 424/115 |
| 5,693,327 | 12/1997 | Shah . |
| 5,916,573 | 6/1999 | Spiers et al. . |

FOREIGN PATENT DOCUMENTS

| | | |
|---|---|---|
| 26 54 743 | 6/1978 | Germany . |
| 688 787 | 3/1998 | Switzerland . |

OTHER PUBLICATIONS

WPI abstracts, section Ch, Week 199710, Derwent Publications Ltd., Class B05, AN 1997–103645, XP002131419 & JP 08 337520A, Tanaka, T. 1996.
Printed advertisement for Occlusal–HP, www.genderm.com, GenDerm Corporation, 1996.
Copy of label and instructions for DuoFilm, Schering–Plough HealthCare Products, 1995.
Brochure for DuoFilm, Schering–Plough HealthCare Products, Inc., 1996.
Principles and Practice of Pediatrics, Second Edition, J.B. Lippincott Company, 1994, Chapter 35, p. 903.
Atlas of Pediatric Dermatology, Lumps and Bumps, Wolfe, 1993, pp 5.5–5.7.
Color Textbook of Pediatric Dermatology, Second Edition, Viral Infections, Mosby, 1996, pp. 121–127.
Rudolph's Pediatrics, 20th Edition, Viral Infections, Simon & Shuster Company, 1996, p. 937–938.
Textbook of Pediatric Infectious Diseases, Edition, 4, vol. 1, Viral and Fungal Skin Infections, W.B. Saunders Company, 1998, pp. 759–763.
Database CAPLUS on STN, AN 1996:226082, abstract of JP 08026980, 1996.
Database Medline on CAS, European Journal of Cancer Prevention, Dwivedi et al., 'Chemopreventive effects of sandalwood oil on skin papillomas in mice,' abstract, 6(4):399–401, Aug. 1996.

*Primary Examiner*—Thurman K. Page
*Assistant Examiner*—Alysia Berman
*Attorney, Agent, or Firm*—Standley & Gilcrest LLP

[57] ABSTRACT

The present invention provides a method for the prevention and treatment of viral-induced tumors, more specifically, human warts. The method uses sandalwood oil and/or derivatives from the sandalwood oil to prepare medicaments for the prevention and treatment of viral-induced tumors (i.e., warts caused by the human papillomavirus (HPV)) in humans. The method of the invention comprises the topical administration of the sandalwood oil or a composition derived therefrom to the human epidermis and/or to the genital tract as needed. The present invention is also concerned with a unique antiviral composition useful for topical application. The antiviral composition according to this invention is also effective against other DNA viruses such as the DNA pox virus that causes *Molluscum contagiosum* and may be effective against other DNA viruses such as AIDS virus and RNA viruses. The sandalwood oil compositions are also effective against genital warts and HPV of the genital tract and will prevent cancer of the skin and cervix.

6 Claims, No Drawings

USE OF SANDALWOOD OIL FOR THE PREVENTION AND TREATMENT OF WARTS, SKIN BLEMISHES AND OTHER VIRAL-INDUCED TUMORS

PRIORITY DATA

This application is a continuation-in-part of U.S. Ser. No. 08/960,303 filed Oct. 29, 1997, now U.S. Pat. No. 5,945,116, which claimed the benefit of U.S. Provisional Application No. 60/030,307 filed Nov. 5, 1996.

TECHNICAL FIELD

The present invention generally relates to prophylactic and therapeutic agents for the prevention and treatment of viral-induced tumors, such as warts. In one embodiment, the therapeutic agent is in the form of a soap, comprising natural sandalwood oil and vegetable ingredients. More specifically, the therapeutic agent is sandalwood oil or an isolate or isolates from the sandalwood oil described herein. Use of the oil or its components as a topical agent for the prevention and treatment of viral-induced tumors, such as human papillomavirus-induced tumors, is disclosed.

BACKGROUND OF THE INVENTION

Viruses which induce tumors in mammals are widespread. Indeed, there are over sixty known types of human papillomaviruses (HPV) which are DNA viruses. These viruses can induce the production of tumors. Some of these HPV's have been associated with benign tumors, such as common warts, while others have been strongly implicated as etiologic agents in dysplasia and carcinomas in the oral and genital mucosa of the infected mammal.

Warts are a very common skin lesion in humans and are caused by various human papillomaviruses (DNA virus). Each virus is related to a specific clinical presentation of the wart. Warts are infectious and can be autoinoculated and spread to other individuals by direct contact.

Verrucae warts have a rough surface, are lumpy and typically flesh colored. Finger-like projections and sometimes dark specks are present, which are the result of thrombosed capillaries. Usually these warts are found on the face and scalp. Plantar warts are found on the planter surface of the feet and can be deep and painful. These warts occur singularly, in clusters or be spread over a wide area. Flat warts are typically small, flat-topped, flesh colored papules that occur primarily on the face, hands and forearms. Usually the surface of the wart is smooth and they may appear in the hundreds. Genital warts are soft, flesh colored or slightly pigmented and occur in the genitalia of the mammal and are sexually transmitted. Chronic infections of the viruses that cause genital warts in women are a serious problem as intra epithelial neoplasia or squamous cell carcinoma may develop. See Oski et al., *Princ. Pract. Pediatrics*, 2nd ed., pp. 789–790.

There are various therapies for the treatment of warts, but none are considered truly effective as they typically fail to totally cure the lesions and do not prevent recurrence. A discussion of presently accepted therapies can be found in Stone, 1995, *Cl. Infec. Diseases*, Suppl. 20, pp. 991–997 and Sterling, 1995, *Practioner*, Jan. 239(1546), pp. 44–47. Numerous compositions are presently marketed for wart removal. One such product is Occlusal®-HP marketed by the GenDerm Corporation of Lincolnshire, Ill. This product is a 17% solution of salicylic acid in a polyacrylic vehicle. The Shering-Plough Company of Memphis, Tenn. produces and markets a product known as Duo Film® which is a patch containing salicylic acid. The product literature recommends that the wart be washed and dried prior to the application of a medicated patch which contains 40% salicylic acid. This patch is then covered with an additional bandage and the procedure is repeated every 48 hours until the wart is gone, which sometimes takes up to 12 weeks.

Recently, it has also been observed that individuals with depressed immune systems, such as sufferers of Acquired Immune Deficiency Syndrome (AIDS), are prone to HPV infections which can result in tumor growth over their entire bodies, resulting in great mental and physical distress to the afflicted individual.

Current modalities for the treatment of viral-induced tumors involve the removal of the tumor by either: (1) surgical intervention (laser or operative); (2) the application of organic acids, such as glacial acetic acid and/or salicylic acid and lactic acid to "burn" the tumor away; (3) the injection into the tumor of an anti-tumor vaccine prepared from ground tumors; and to a lesser extent, (4) the use of a drug, such as podophyllin, interferons and fluorouracil or 5-FU; and (5) freezing.

While being useful for removing the viral-induced tumor, the current treatment modalities still suffer from one or more of the following drawbacks: (1) they can result in the destruction of healthy uninfected tissue; (2) they can result in scarring and disfigurement; (3) they can result in discomfort to the mammal being treated thereby; (4) they can result in necrosis of the tumor and the surrounding tissue may can result in a secondary infection which may require treatment with an antibiotic; and (5) they do not always result in the destruction of latent viral DNA which may be maintained in surrounding tissues. Furthermore with these conventional treatments, subjects suffer from significant local, and at times, systemic side effects, incomplete resolution and frequent recurrences of the tumors, and of course, the expense incurred.

It is also known that phototherapy is used for removing laryngeal papillomatosis tumors. While such phototherapy reduces tumor growth by about 50%, it also results in a generalized skin photosensitivity for at least six weeks, as well as other minor reactions. Despite the apparent success of this technique, the presence of latent viral DNA is nonetheless still maintained in the surrounding tissues.

U.S. Pat. No. 5,073,630 discloses a polymeric anhydride of magnesium and ammonium phospholinoleate with antiviral, antineoplastic and immunostimulant properties. This antiviral agent is produced from a selected line of Aspergillus sp. However, the compound is insoluble in water and possesses a high molecular weight (316,000 daltons). Recovery of the compound from the culture is problematic and costly.

U.S. Pat. No. 5,562,900 discloses a composition for the treatment of viral-induced tumors comprising an Aspergillus fermentation extract or a derivative thereof in a pharmaceutically acceptable carrier.

U.S. Pat. No. 5,541,058 discloses an in vitro method for testing the effectiveness of antiviral agents. More specifically, this patent relates to a method for screening anti-papillomavirus drugs which can interfere with the early and maintenance stages of papillomavirus infection. The teachings of this patent are incorporated herein by reference.

U.S. Pat. No. 5,332,215 discloses a method for inhibiting viral proliferation by preventing or inhibiting viral replication or killing the virus on contact. The method uses serine protease inhibitors, their analogs, salts, conjugates or derivatives.

An article by B. M. Lawrence entitled "Progress in Essential Oils", *Perfumer & Flavorist,* Vol. 16, 49–58 (1991) reviews the work of several investigators on the chemical composition of sandalwood oil. This article reports on several of the oxidation products of the oil and compares the composition of Chinese sandalwood oil and Indian sandalwood oil. The santalol content (santalol, cis-α and cis-β, comprises about 50 and 20% respectively by weight of sandalwood oil) of various species of the genus Santalum, are also disclosed. This article makes no suggestion that sandalwood oil would be effective in treating the common wart in humans.

An article by Dwivedi et al. entitled, "Chemopreventive effects of sandalwood oil on skin papillomas in mice" in the *European Journal of Cancer Prevention* 1997; 6(4): 399–401, reports that the essential oil, emulsion or paste of sandalwood (*Santalum album* L) has been used in India as an ayruvedic medicinal agent. In his investigation, a 5% w/v solution of sandalwood oil in acetone was shown to be a chemopreventive agent against 7, 12-dimethylbenz(a) anthracene initiated and 12-O-tetracecanoyl phorbol-13-acetate promoted skin papillomas in CD1 mice. The author suggests that sandalwood oil could be an effective chemopreventive agent against skin cancer.

None of these references suggest or disclose the use of sandalwood oil or a soap containing sandalwood oil as an agent for the treatment of human papillomavirus-induced tumors. There presently exists in the medical community a need for improved methods and compositions which provide prophylactic and/or therapeutic treatment of viral-induced tumors such as warts in humans. The present invention fills that need of the medical community.

SUMMARY OF THE INVENTION

One aspect of the present invention relates to the use of at least one constituent of sandalwood oil or a soap containing sandalwood oil for the prevention and treatment of viral-induced tumors. Another aspect of the invention relate to the use of a component or components of said oil to prevent and treat viral-induced tumors in mammals, especially humans. One major benefit of the present invention is that that oil and soap do not destroy healthy, uninfected tissues nor results in either significant systemic side effects, local side effects such as irritation, necrosis of tissue surrounding the wart, allergic rashes, scarring, disfigurement or discomfort to the human treated therewith. In fact, the use of sandalwood oil or a soap containing the oil has been found to smooth the patient's skin and provide for regeneration of healthy tissue.

Another aspect of the present invention is directed to a simple method for providing prophylactic and therapeutic treatment of viral-induced tumors in humans. An additional aspect of the present invention relates to a method for the destruction of latent viral DNA which is contained in tissues so as to prevent recurrence of these tumors.

Thus, there is disclosed a method for the prevention and treatment of viral induced tumors and skin cancers in a mammal, said method comprising the topical application of sandalwood oil.

Also disclosed is a prophylactic and therapeutic composition for the prevention and treatment of viral induced tumors in mammals comprising sandalwood oil extract, or a derivative thereof, in a pharmaceutically accepted carrier and wherein said sandalwood oil extract is obtained from a Santalum species selected from *S. album, S. yasi, S. papuanum, S. spicatum* and mixtures thereof.

There is further disclosed a method for the prevention and treatment of genital warts, cancer of the cervix and eradication of human papillomavirus from the female genital tract in infected females, comprising the application of a cream or douche derived from at least one constituent of sandalwood oil to the affected area of the human body. There is also disclosed a method for preventing cancer of the cervix, said method comprising the application of sandalwood oil to the genital area of a female for a period of time and at a sufficient concentration to eradicate the human papillomavirus from the genital area of the female. There is also disclosed a method for the treatment and prevention of dry skin, flakiness of the skin, rashes associated with seborrheic dermatitis, psoriasis, eczematous and allergic rashes in a human, said method comprising the topical application of a composition comprising at least one constituent of sandalwood oil to the skin of said human.

The method of this invention is specifically directed to the use of a composition that is suitable for topical application. The initial discovery of the inventors was based upon the use of a soap manufactured by Karnataka Soaps & Detergents, Ltd., Bangalore, India, known and marketed as "Mysore Sandal Soap". The product packaging states that this soap contains natural Mysore sandalwood oil distilled by the government of Karnataka. It is known that this soap also contains vegetable ingredients. A second soap manufactured by Alfa Cosmetics, of Bombay, India, known as "Eastern Mysore's Pure Sandal Soap" has also been found effective in preventing and/or treating viral induced epidermal tumors, however, it is somewhat less effective. The "Eastern Mysore's Pure Sandal Soap" lists as its ingredients: palm stearin, rice bran fatty, coconut oil, caustic soda, perfume, sandalwood oil and preservatives. At the time the parent patent application was filed, the inventors had not isolated the active component from the sandalwood soap. However, at the time of filing the present application, the inventors, through further investigative effort, have determined that the sandalwood oil component of the soap was responsible for its prophylactic and therapeutic effects. As of the filing date of this application, the inventors are working towards the isolation of the active ingredient or active ingredients from the sandalwood oil. As used herein and in the claims, the term "sandalwood oil" shall mean: (1) the actual oil derived from the Santalum plant and/or (2) the active component or components (constituents) of said oil.

Sandalwood oil is a pale yellow, somewhat viscous, aromatic liquid obtained from sandalwood and is used chiefly in perfumes and soaps. Sandalwood is a close grained, fragrant, yellowish heartwood of a semi-parasitic plant of the genus Santalum (family Santalaceae), especially the fragrant wood of the true or white sandalwood, *Santalum album.* Approximately ten (10) species of Santalum are distributed through southeastern Asia and the islands of the South Pacific. The oil is obtained by steam distillation of the wood. Palm stearin or palm oil is an edible fat obtained from the flesh of the fruit of several palms and is typically used in soaps and lubricating greases. More particularly, palm stearin is a fraction of palm oil. Palm oil typically contains the fatty acid palmitic acid, which is a waxy, crystalline saturated fatty acid having the formula $C_{16}H_{32}O_2$ and may exist in the free acid form or in the form of esters (as glycerides) and most fats and fatty oils, and in several essential oils and waxes. Stearic acid ($C_{18}H_{36}O_2$) is one of the most common fatty acids and occurs and glycerides in most animal and vegetable fats, particularly in the harder fats with high melting points. A solid mixture of stearic and palmitic acids, "stearine", is used for making candles. The soaps are the sodium and potassium salts of stearic and palmitic acids.

One sandal soap listed rice bran fatty as an ingredient. Grains of cereals, such as rice and wheat, have a great deal in common with each other. They consist of three major structures: (1) the embryo or germ of the new plant; (2) the endosperm, which is the storer of nutrients for the germinating plant; and (3) the protective layers of the seed coat, which are regarded as bran by the miller. A typical bran composition (wheat on a dry weight basis) is: lignin-8%, cellulose-30%, hemi-cellulose-25%, starch-10%, sugars-5%, protein-15%, lipid-5%, and inorganic and other substances making up the remainder. It is believed that the rice bran fatty component of the sandal soap is in fact the lipid component from rice bran. It is further believed that there are a number of fatty acids with unusual structures that are found in rice bran. One such fatty acid is ricinoleic acid. Coconut oil is a fatty acid oil or semi-solid fat extracted from fresh coconuts and is used especially in making soaps and food products. The fatty acid composition of coconut oil is predominantly lauric acid. The composition of coconut oil has been thoroughly characterized and is known in the art. Caustic soda, also known as sodium hydroxide, is well known to be used in the production of soaps and detergents.

Other components such as preservatives and perfumes can be used in the sandal soaps of this invention. At this time, the complete characterization of those components are not available to the inventors. However, continued analysis has determined that the active component or components in the soap is the sandalwood oil. As will be set forth below, the inventors have elucidated that the sandalwood oil is the agent with the outstanding utility for treating or preventing human warts. In any event, as will be demonstrated below, it has been discovered that sandal soap and sandalwood oil is very effective in treating human warts.

The major components or constituents of sandalwood oil are cis-α-santalol and cis-β-santalol, about 50 and 20 weight % respectively. While any source of sandalwood oil is effective in the present invention, the Indian oil is preferred. Oxidation products may also be present in the oil, such as β-santalic acid and α-tetrasantalic acid. Table I sets forth the constituents of a fresh sandalwood oil and an old oil.

TABLE I

Comparative composition of "Fresh" and "Old" Samples of Sandalwood Oil

| Compound | Weight Percentage Composition | |
| --- | --- | --- |
|  | Fresh Oil | Old Oil |
| santene | 0.01 | 0.05 |
| α-pinene* | — | 0.02 |
| camphene* | — | 0.02 |
| acetic acid | — | 0.02 |
| teresantalal | — | 0.04 |
| α-santalene | 0.82 | 1.30 |
| trans-α-bergamotene | 0.12 | 0.11 |
| epi-β-santalene | 0.97 | 1.40 |
| β-santalene | 1.40 | 1.90 |
| γ-curcumene | 0.04 | 0.06 |
| β-bisabolene | 0.07 | — |
| β-curcumene | 0.13 | — |
| α-eka-santalal | 0.07 | 0.49 |
| ar-curcumene | 0.26 | 0.55 |
| β-eka-santalal | 0.01 | 0.19 |
| (E)-nerolidol | 0.06 | — |
| β-bisabolol | 0.64 | 0.04 |
| α-santalal | 2.90 | 7.70 |
| (Z)-trans-α-bergamotal | 0.10 | 0.30 |
| α-bisabolol | 0.26 | — |
| cis-α-santalyl acetate | — | 4.40 |

TABLE I-continued

Comparative composition of "Fresh" and "Old" Samples of Sandalwood Oil

| Compound | Weight Percentage Composition | |
| --- | --- | --- |
|  | Fresh Oil | Old Oil |
| β-santalal | 0.56 | 1.80 |
| dihydro-α-santalol | 0.38 | — |
| cis-β-santalyl acetate | — | 2.50 |
| cis-α-santalol | 50.00 | 22.00 |
| (Z)-trans-α-begamotol | 3.90 | 1.30 |
| nuciferyl acetate⁺ | — | 0.33 |
| trans-α-santalol | 0.56 | .040 |
| epi-β-santalol | 4.10 | 2.10 |
| cis-β-santalol | 20.90 | 9.80 |
| trans-β-santalol | 1.50 | 0.79 |
| cis-lanceol | 1.70 | 0.29 |
| cis-nuciferol | 1.10 | 0.75 |
| spirosantalol | 1.20 | 0.47 |

*presumed impurities
⁺probably cis-nuciferyl acetate

The chemical make-up of a sandalwood oil varies slightly from source to source, however, α- and β-santalol make up over 65% of the oil. Table II sets forth the chemical make up of Chinese and Indian oils.

TABLE II

Comparative chemical composition of Indian and Chinese sandalwood oil

| Compound | Percentage Composition | |
| --- | --- | --- |
|  | Chinese Oil | Indian Oil |
| tricyclo-eka-santalal | 0.63 | ca 0.30 |
| α-santalene | 0.68 | 1.13 |
| trans-α-bergamotene | ca 0.50 | ca 0.10 |
| β-santalene⁺ | 0.93 | 0.35 |
| β-santalene⁺ | 1.37 | 0.63 |
| ar-curcumene | 0.43 | ca 0.50 |
| α-santalol⁺ | 49.99 | 48.44 |
| β-santalol⁺ | 3.78 | 4.19 |
| β-santalol⁺ | 18.12 | 24.57 |
| nuciferol⁺ | 3.14 | 5.45 |
| β-santalal | 3.44 | 1.91 |
| α-santalal | ca 0.20 | 0.53 |

The santalol content also varies slightly from species to species of Santalum. Table III sets forth the santalol content of various Santalum species.

TABLE III

Santalol content of various Santalum species

| Santalum Species | Origin | Percentage composition | |
| --- | --- | --- | --- |
|  |  | α-santalol | β-santalol |
| S. album (1)* | China | 14.6 | 7.3 |
| S. album (4) | India | 46.6–59.9 | 24.6–29.0 |
| S. album (5) | Indonesia | 7.1–48.6 | 8.7–25.2 |
| S. yasi (1) | Fiji | 54.0 | 32.8 |
| S. papuanum (1) | Papua, New Guinea | 26.3 | 15.5 |
| S. spicatum? (3) | Australia | 27.9–35.3 | 4.0–29.2 |
| unknown (1) | India | 3.0 | 10.8 |

*No. of samples

In a further embodiment of this invention, the method of preventing or treating viral-induced tumors uses sandalwood oil that is in a pharmaceutically acceptable carrier such as oleaginous ointment for topical administration.

In another embodiment of this invention, the active component or components of the sandalwood oil are disclosed for the prevention or treatment of viral-induced tumors.

There is further disclosed a prophylactic and therapeutic composition for the prevention and treatment of viral-induced tumors in mammals comprising sandalwood oil extract thereof or a derivative thereof in a pharmaceutically acceptable carrier.

In particular, the sandalwood oil itself and/or the extracts (active components) of the oil described herein are used for the preparation of prophylactic and therapeutic compositions for the treatment and prevention of viral-induced tumors in humans. Preferably, the compositions useful in the method are topically applied to the human in need of such therapy.

The method of the present invention neither destroys healthy, uninfected tissue nor results in any local or systemic side effects, scarring, disfigurement or discomfort to the human treated. Furthermore, the use of the present method results in the destruction of latent viral DNA found in the tumor and the surrounding tissues so that instances of incomplete resolution and tumor recurrence are prevented. The method includes the use of the sandalwood or an extract derived therefrom, for the administration to an area of the human which is anticipated to evidence viral-induced tumor growth, or an area which presently exhibits viral-induced tumor growth (i.e., warts) to prevent or eliminate the viral-induced tumor. In accordance with the method according to this invention, "regular use of the sandalwood oil" is meant to mean application of the sandalwood oil at least once a day to the body surface containing the wart(s). A further embodiment of the method of this invention comprises washing the affected area of the body with the soap, rinsing the area and then placing a small amount of soap residue or oil on the tumor to be treated. It has been determined through clinical evaluation that once the method of this invention is initiated, the warts begin to shrink, no matter what size, and will totally disappear after a period of two to four weeks of treatment, or less if the oil is applied.

DESCRIPTION OF PREFERRED EMBODIMENTS

The present invention is based, in part, on the discovery that a commercially available soap manufactured by the aforementioned companies is useful for the treatment of viral-induced tumors in humans. More specifically, the invention is directed to the discovery that sandalwood oil is the active component of the soap.

The initial chemical analysis was conducted as follows. 2.5 g of the sandal soap was dissolved in 15 ml of purified water. The pH was determined to be about 10.26. This solution was extracted, after acidification, with methylene chloride. The methylene chloride extract was dried over sodium sulfate and the volume was adjusted to 40 ml. The extract was diluted 10-fold and subjected to Gas Chromatography Mass Spectrometry (GC-MS) analysis. The analysis was performed on a Finnigan Model 4500 GC/MS system equipped with an HP-5890 Series II gas chromatograph and Galaxy 2000 data system. The semi-volatile GC column was a 30 meter by 0.32 mm RTX-5 capillary column. The temperature of the column was held at 40° C. for 1 minute, and then increased at 10° C./minute to a final temperature of 270° C.

Conversion of the hydroxide ion concentration was carried out using the definition of pH ($-\log[OH^-]=14-pH$). It was determined that the concentration of sodium hydroxide equivalents was about 0.015% by weight.

GC-MS analysis confirmed that no salicylic acid was present, a known agent for the treatment of warts. The fatty acids, dodecanoic, tetradecanoic, hexadecanoic, oleic and octadecanoic, were present. The weight ratio of dodecanoic; tetradecanoic; hexadecanoic; oleic; octadecanoic was 7:3.4:50.1:32:6.7. The ratio of hexadecanoic acid to oleic acid in palm oil is about 34 to 43% hexadecanoic acid to about 38 to 40% oleic acid. This analysis indicates that the soap was most likely derived from palm oil.

No other peaks were evident from this GC-MS analysis of the methylene chloride extract of the sandal soap at a detection limit after dilution of 1% by wt. As set forth below, the components of the sandalwood oil were found effective against human viral-induced tumors.

EXAMPLE 1

One inventor of the present invention is a pediatrician, actively engaged in the medical practice. Typically, pediatricians are constantly exposed to the HPV, which causes warts in humans. The inventor has had numerous occurrences of warts over the last 10 years, for which all available methods of treatment have been used, including excision using liquid nitrogen and various salicylic acid preparations. All of these methods of treatment failed to completely eradicate the warts. Typically, the warts became secondarily infected and were very painful. With conventional treatment, the warts subsided, however they only returned after a period of time. This inventor also developed a painful wart in between her fourth and fifth toes of her right foot which were scraped and then treated with commercially available creams known as Vytone and Lachydrin by a Dermatologist. Despite continued treatment, the warts recurred and were a constant source of aggravation. The inventor also developed a large wart on her left thumb, about 3 mm in diameter with dark spots on the surface. Subsequent to the appearance of the wart on the thumb, Mysore Sandal Soap was obtained and, after 4 to 5 days of use (washing twice daily), the wart on the thumb became smaller (appeared to shrink), reduced down to about 2 mm in diameter and continued to decrease in size until it completely disappeared after three weeks of treatment.

The inventor then began to wash (twice daily) the wart on her foot, which at the beginning of therapy was about 5 mm in diameter. After one week of daily applications of the sandal soap, the pain of the tumor had decreased and the wart was beginning to shrink in size. After a second week of washing and rinsing the tumor with the sandal soap, the inventor began to leave a small amount of soap residue on the affected area. No irritation or redness resulted from the soap residue and the tumor continued to decrease in size and totally disappeared after the third week of such usage.

EXAMPLE 2

A second individual, a four (4) year old black female, presenting a huge (about 4 mm), raised, wart on her right hand, began treatment of the wart with sandal soap. After about two weeks of treatment, (washing twice a day), the tumor had reduced to a small black dot and at the third week of treatment, the tumor was completely gone.

EXAMPLE 3

A seven (7) year old white male presented warts on each foot; one being about 3 mm in diameter, with raised dark spots on the surface and the other about 4 mm labulated and flesh-colored. These tumors were washed twice daily with the sandal soap. After one week of therapy, the tumors were visibly smaller and at that time, soap residue was allowed to remain on the tumor and surrounding tissue after washing. After two weeks, the tumors were completely gone and no new tumors were evident.

EXAMPLE 4

A ten (10) year old white female presented a large, 3 mm raised and fleshy wart on the dorsum of her right hand. Administration of the sandal soap began and after two weeks of treatment, the tumor shrunk to approximately half its size.

EXAMPLE 5

5 grams of the Mysore Sandal Soap was dissolved in 15 ml of distilled water. The pH of the solution was adjusted to 5.5 with HCl and this mixture was then extracted with methylene chloride. The methylene chloride extract is dried and the volume reduced to about 20 ml. This methylene chloride extract is then topically applied to a human wart. Application is to occur twice daily. After one to two weeks of treatment, the viral-induced tumor will have been eliminated.

EXAMPLE 6

Equal parts by weight of rice bran fatty acids and sandalwood oil is prepared. A cream suitable for topical use is prepared by mixing 1 gm of the rice bran/sandalwood oil composition with 20 gms of a balm, which comprises a mixture of petrolatum, mineral oil and wood alcohol. The cream is useful for minor irritations and in the treatment of viral infections which produce skin lesions or warts.

EXAMPLE 7

A third year medical student who had recurrence of plantar warts after surgical removal, used the sandal soap for four (4) weeks for washing the warts and was told to leave a small residue of soap on the warts after washing. The warts started shrinking as early as the first week and they totally disappeared after the fourth (4th) week and have not recurred.

EXAMPLE 8

A sixteen (16) year old white male subject presented a plantar wart on the foot that had recurred after surgical removal. The subject began using the sandal soap and after a period of about 3 weeks, the wart was totally gone and has not recurred. This subject washed the plantar wart with the sandal soap at least twice daily.

EXAMPLE 9

A third year, white, female medical student presented warts on her fingers. She had previously used salicylic acid preparation, but the warts had recurred. After use of the sandal soap, twice daily for about 1 week, the warts started shrinking and in about three (3) weeks, the warts totally disappeared and have not recurred.

EXAMPLE 10

One adult white male had chronic seborrheic dermatitis on the face and scalp. Upon daily administration of the sandal soap to the scalp and face, a significant improvement in his dermatologic condition was obvious. He found sandal soap was more effective in treating his condition than expensive shampoos and steroid creams which he previously used.

EXAMPLE 11

An adult white male and female presented psoriasis lesions on hands and arms. After approximately 1 week of treatment with the sandal soap, great improvement in this condition resulted. Twice daily applications of the sandal soap to the affected areas, significantly reduced flaking and dryness. The use of expensive steroid creams was significantly reduced by these subjects as the sandal soap therapy significantly reduced the psoriasis lesions. This soap could also be beneficial for allergic and eczematous rashes.

EXAMPLE 12

A fifty (50) year old white female presented with a plantar wart embedded inside a callous on her right foot which had recurred after several treatments which included surgical removal, freezing, etc. by a dermatologist. After about four (4) weeks of treatment with the sandal soap, the wart was totally gone and so was the pain and discomfort, which disappeared after the total resolution of the deeply embedded plantar wart on her right foot.

At the time of filing this application, further clinical work is underway to refine the method of the present invention and to further characterize the active components of the sandalwood oil.

At this time, a total of fifteen (15) individuals have undergone the inventive therapy and all 15 experienced the eradication of their palmar or plantar warts. The application of the sandal soap at least twice daily with occasional placement of soap residue on the warts, results in disappearance of the warts in about four (4) weeks. Deeply embedded warts took up to eight (8) weeks to resolve. Of the 15 individuals treated to date, twelve (12) were previously treated with salicylic acid preparations, liquid nitrogen or surgical techniques. In all twelve (12) cases, the warts reappeared. Upon reappearance of the warts, the subjects enrolled into the sandal soap study and have successfully completed their course of therapy and the warts have failed to reappear. It was noted that the individuals that had previously received salicylic acid treatments were slower to respond to the inventive therapy when warts were covered by scar tissue. However, in all cases, the warts had disappeared within four (4) to eight (8) weeks and recurrence of warts had not yet been detected.

EXAMPLE 13

*Molluscum contagiosum* is a skin disease caused by DNA pox virus and is characterized by the appearance of small, discreet lesions, in groups, on the face, arms or genitalia. The lesions are firm and pearly white with a sharply indented central core and yield an infectious filtrate which produces the disease when inoculated into human volunteers. The disease, which may be epidemic in children, occurs in all ages and is world-wide in distribution. Two subjects with *Molluscum contagiosum* were treated for about four (4) weeks using the sandal soap of the present invention. One of them had about twenty-five (25) large and small lesions. Some of the lesions were greater than 1 cm in diameter; the smaller lesions were about 5 mm in diameter. Application of the sandal soap occurred at least once per day, with a small amount of soap left behind on the lesions and the lesions disappeared in about four (4) weeks. The lesions failed to reappear since resolution.

EXAMPLE 14

The sandal soap according to the invention has also been found effective against the flaky rashes of psoriasis to seborrheic dermatitis, eczematous rash and dry skin. Individuals with the above recited conditions, upon use of the sandal soap, experienced a considerable decrease in itching, redness and flakiness subsequent to the use of the sandal soap. Also, the use of steroid creams was considerably reduced when the sandal soap was used in the management of the above recited rashes.

EXAMPLE 15

Adolescents and adults presented with facial acne and were instructed to use the sandal soap on a regular, daily basis. After about two (2) weeks of therapy, the presence of facial acne had decreased significantly or disappeared. Sandal soap was effective in eradicating pustular acne also. This work evidences that the sandal soap has anti-bacterial characteristics also which indicates its efficacy towards the control of Streptococcus and Staphylococcus skin infections.

EXAMPLE 16

A pediatrician colleague of the inventors, who had palmar warts for the last fourteen (14) years that kept recurring after the available, conventional treatment for warts, including use of salicylic acid preparation, used sandal soap for five (5) weeks with total resolution of the palmar wart that has not recurred.

EXAMPLE 17

A 27 year old married female with an abnormal pap smear due to HPV, as per her gynecologist, used sandal soap to wash her genital area whenever she took her bath and also sat in soapy water from sandal soap in her bathtub at least a couple of times per week. When the pap smear was repeated six (6) months later, it is reported to be normal and the HPV was not detected.

EXAMPLE 18

A 46 year old Asian female presented with almost innumerable warts on both heels. The subject had endured these warts for over seven (7) years and the standard therapies of freezing, cutting, salicylic acid the like (administered by a Dermatologist) had failed to resolve the malady. The Dermatologist informed the patient that her condition was not subject to the standard therapies and that she had to learn to live with these warts. Prior to the time the sandalwood oil treatments began, the patient was forced to cut the warts so that walking across a carpet was possible. The patient experienced pain and embarassment due to the numerous warts.

At the initial examination, the warts were very large, pigmented and painful. The skin around the warts was very dry with heavy callous formations. The left heel had 36 warts, one of them having dimensions of 1.4 cm by 8 mm and 6 mm in height. A second large wart measured 0.8 cm by 0.8 cm and was 5 mm in height. The remaining warts were in the range of 3–4 mm in diameter and height. The right heel had at least 40 warts with one very large wart that measured about 1 cm by 6 mm and about 4 mm in height. The remaining warts were 4–5 mm by 3–4 mm and 2–3 mm in height.

The patient also presented with 3 warts on her left hand which had returned after the standard treatments of freezing, cutting and use of salicylic acid had failed to resolve the condition. 2 warts were on her index finger and measured about 0.5 cm by 4 mm by 2 mm. One wart was on her thumb and measured about 3 mm by 2 mm by 2 mm.

The patient was supplied about 10 cc of pure (not diluted) Indian sandalwood oil. The patient was instructed to wash the tumors prior to application of the oil and to use a pumice stone on her heels to remove the calluses and dry skin. A drop of oil was placed on each lesion and rubbed on the wart each evening prior to retiring to bed. Therapy began on Jul. 12, 1998.

At the first follow-up visit on Jul. 23, 1998, the warts on the left hand had disappeared. The patient stated that within a few days of beginning treatment, the warts darkened and then scabbed over. By the eleventh day of therapy, the warts on her hand had disappeared, except that a small dark spot (scab) remained on the thumb.

Out of the 36 warts on the left heel, 26 had disappeared while the remaining 10 were totally flattened with dried residual wart tissue at the site of the wart. 30 out of the 40 warts on the right heel had resolved and disappeared. The remainder were flat with residual dried wart tissue.

A second follow-up exam took place on Jul. 29, 1998 and it was observed that the small dark spot on the left thumb was gone as were the remaining warts on the right heel. The right heel was smooth and shiny and completely free of warts. The left heel was clear of tumors except that 3 small areas still existed with dried wart tissue. The patient and inventors were very pleased with the rapid (about 2½ weeks) elimination of the warts and are convinced that the sandalwood oil is a highly effective antiviral and antimitotic agent.

In light of these results, the inventors have concluded that sandalwood oil (or a component of the oil) is not only an antiviral agent against HPV, DNA pox virus and perhaps other viruses but it would also be a chemoprotective agent for skin cancers and an effective therapy for cancerous or precancerous lesions of the skin and the female genital tract.
Other Indications Since warts are caused by human papillomaviruses (HPV) of different types and the sandalwood oil disclosed herein can eradicate this virus, it is contemplated that this composition may be useful in methods of eradicating other viral-induced tumors. Genital warts are also caused by HPV. Genital warts in women are a genuine nuisance and are very hard to eradicate. The sandalwood may also be useful to prevent other DNA viral lesions. Its effect on other DNA as well as RNA viruses needs further investigation. The fact that sandalwood oil appears to be extremely effective in eradicating palmar and plantar warts caused by the DNA HPV virus and also effective in treating *Molluscum contagiosum* rash caused by DNA pox virus supports its effectiveness against other DNA and RNA viruses.

It is proposed that the continued use of sandalwood oil or the components of sandalwood oil (such as α- and β-santalol) would be effective for the prophylactic treatment of viral tumors and eradication of DNA viral infections and bacterial infections caused by streptococci or staphylococci.

During the clinical evaluation of the present invention, it has come to the attention of the inventors that the sandalwood oil, sandal soap and/or the effective components of the sandalwood oil are also very effective in preventing dryness of the skin. As mentioned in Example I, an inventor of the present application is a pediatrician and is constantly (i.e., at least 40 times per day) washing her hands after examining a subject. This constant washing with soaps as required in a hospital setting, results in severe dryness to the hands. The sandal soap was applied twice a day to the dorsum of her left hand. The sandal soap was not applied to the dorsum of her right hand while washing her hands. At the end of approximately two weeks, the skin on the dorsum of her left hand was smooth, soft and shiny which was in contrast to the dry rough skin on the top of her right hand.

Thus, the sandal soap and sandalwood oil described herein has also been found effective in preventing the flakiness and dryness associated with skin that is constantly subject to harsh detergents. In addition, the sandal soaps have shown to be active against seborrheic dermatitis and psoriasis.

From the studies disclosed herein, sandalwood oil demonstrated specific antiviral properties against HPV, DNA pox virus that causes *Molluscom contagiosum* and is also effective in the treatment of bacterial skin infections. The properties of sandalwood oil also include anti-inflammatory characteristics as it has demonstrated effective emollient properties for dry skin and psoriasis.

It is quite evident from the clinical experience to date, that the sandalwood oil of the present invention has been outstandingly effective in the treatment and elimination of warts. The complete eradication of the warts with no recurrence is truly a surprising result as the medical community still searches for a cost effective and efficacious method to control this human malady.

INDUSTRIAL APPLICABILITY

Viral-induced tumors, especially of the skin, are very common. These tumors are typically very difficult to treat, control and prevent. The medical community has searched for decades for new therapies to treat this common human malady. The present invention provides a simple and cost-effective method to treat and prevent these viral-induced tumors.

As mentioned above, the term "sandalwood oil" is meant to include the oil itself, and any active component or components that are isolated therefrom. At the time of filing this patent application, the inventors are diligently pursuing the isolation of the active component or components and believe that such can be accomplished without excessive experimentation.

Many modifications may be made to the invention herein without departing from the basic spirit or scope of the invention. Accordingly, it will be appreciated by those skilled in the art, that within the scope of the appended claims, the invention may be practiced by means other than has been specifically described herein.

We claim:

1. A method for the treatment of human papillomavirus (HPV)-induced tumors in a mammal, said method comprising the topical application of sandalwood oil to said mammal.

2. The method according to claim 1 wherein said (HPV)-induced tumor is selected from the group consisting of verrucae warts, plantar warts, flat warts, genital warts and *Molluscum contagiosum.*

3. The method according to claim 1 wherein said sandalwood oil is obtained from at least one Santalum species selected from the group consisting of *S. album, S. yasi, S. papuanum* and *S. spicatum.*

4. The method according to claim 3 wherein said sandalwood oil is in admixture with a pharmaceutically acceptable carrier or excipient.

5. The method according to claim 1 wherein said sandalwood oil is in admixture with a pharmaceutically acceptable carrier or excipient.

6. A method for the treatment of genital warts, and treatment of human papillomavirus (HPV) from the female genital tract in infected females comprising the application of a cream or a douche comprising sandalwood oil.

* * * * *

UNITED STATES PATENT AND TRADEMARK OFFICE
CERTIFICATE OF CORRECTION

PATENT NO. : 6,132,756
DATED : October 17, 2000
INVENTOR(S) : Haque et al.

It is certified that error appears in the above-identified patent and that said Letters Patent is hereby corrected as shown below:

In Column 3, line 38, please delete the word "relate" and insert the word -- relates --.

Signed and Sealed this

Eighth Day of May, 2001

Attest:

NICHOLAS P. GODICI

Attesting Officer

Acting Director of the United States Patent and Trademark Office